US012357840B2

(12) United States Patent
Jiles et al.

(10) Patent No.: US 12,357,840 B2
(45) Date of Patent: Jul. 15, 2025

(54) DEEP TRANSCRANIAL MAGNETIC STIMULATION APPARATUS AND METHOD

(71) Applicants: David C. Jiles, Ames, IA (US); Magundappa Ravi L. Hadimani, Glen Allen, VA (US); Priyam Rastogi, Ames, IA (US)

(72) Inventors: David C. Jiles, Ames, IA (US); Magundappa Ravi L. Hadimani, Glen Allen, VA (US); Priyam Rastogi, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 74 days.

(21) Appl. No.: 17/952,949

(22) Filed: Sep. 26, 2022

(65) Prior Publication Data
US 2023/0025426 A1    Jan. 26, 2023

Related U.S. Application Data

(62) Division of application No. 15/335,286, filed on Oct. 26, 2016, now Pat. No. 11,547,867.

(60) Provisional application No. 62/250,571, filed on Nov. 4, 2015.

(51) Int. Cl.
*A61N 2/00* (2006.01)
*A61N 2/02* (2006.01)

(52) U.S. Cl.
CPC .............. *A61N 2/006* (2013.01); *A61N 2/02* (2013.01)

(58) Field of Classification Search
CPC .......... A61N 2/00; A61N 2/002; A61N 2/004; A61N 2/006; A61N 2/008; A61N 2/02; A61N 2/12
See application file for complete search history.

(56) References Cited

U.S. PATENT DOCUMENTS

| 5,415,617 | A | * | 5/1995 | Kraus | A61N 2/02 336/122 |
| 5,707,334 | A | * | 1/1998 | Young | A61N 2/02 600/9 |
| 9,254,394 | B2 | * | 2/2016 | Zangen | A61N 2/006 |
| 9,320,913 | B2 | * | 4/2016 | Dimino | A61N 1/40 |

(Continued)

FOREIGN PATENT DOCUMENTS

WO    WO 2016/116747 A1    7/2016

OTHER PUBLICATIONS

A. Rotem et al., "Solving the orientation specific constraints in transcranial magnetic stimulation by rotating fields"; *PLoS One*, vol. 9, No. 2, 2014.
L. J. Crowther et al., "Transcranial magnetic stimulation: Improved coil design for deep brain investigation"; *J Appl. Phys.*, vol. 109, No. 7, p. 078314, 2011.

(Continued)

*Primary Examiner* — Carrie R Dorna
(74) *Attorney, Agent, or Firm* — Reinhart Boerner Van Deuren P.C.

(57) ABSTRACT

A coil configuration and method for transcranial magnetic stimulation enabling stimulation of deep regions of the brain without excessively stimulating the cortex is provided. The coil configuration utilizes at least one coil to produce an off-plane magnetic field to enhance the magnetic field from a top TMS coil. In one configuration at least a single variable position coil referred to as the Variable Halo Coil and positionable vertically and/or angularly is used.

18 Claims, 5 Drawing Sheets
(4 of 5 Drawing Sheet(s) Filed in Color)

(56) References Cited

U.S. PATENT DOCUMENTS

| | | | |
|---|---|---|---|
| 2004/0193000 A1* | 9/2004 | Riehl | A61N 2/006 600/15 |
| 2005/0234286 A1* | 10/2005 | Riehl | A61B 5/684 600/9 |
| 2010/0185042 A1* | 7/2010 | Schneider | A61N 2/004 600/13 |
| 2010/0286470 A1 | 11/2010 | Schneider et al. | |
| 2011/0184223 A1* | 7/2011 | Peterchev | A61N 2/02 600/14 |
| 2011/0273251 A1* | 11/2011 | Mishelevich | A61N 2/006 335/299 |
| 2014/0062379 A1 | 3/2014 | Dai et al. | |
| 2015/0099921 A1* | 4/2015 | Schneider | A61N 2/02 600/14 |
| 2015/0196772 A1* | 7/2015 | Ghiron | A61N 2/006 600/13 |
| 2018/0369601 A1 | 12/2018 | Saitoh et al. | |

OTHER PUBLICATIONS

L. Crowther et al., "Improved transcranial magnetic stimulation coil design with realistic head modeling", *Bull. Am. Phys. Soc.*, vol. vol. 58, No. 1, Mar. 2013.

Y. Meng et al., "Deep brain transcranial magnetic stimulation using variable 'Halo coil' system"; *J Appl. Phys.*, vol. 117, No. 17, p. 178305, May 2015.

S. March et al., "Novel transcranial magnetic stimulation coil for mice"; *Bull. Am. Phys. Soc.*, vol. 59, 2014.

Z. D. Deng et al., "Electric field depth-focality tradeoff in transcranial magnetic stimulation: simulation com arison of 50 coil designs"; *Brain Stimul.*, vol. 6, No. 1, pp. 1-13, Jan. 2013.

Stephen D. March et al., "Thermal and Mechanical Analysis of Novel Transcranial Magnetic Stimulation Coil for Mice"; IEEE Transaction on Magnetics; vol. 50, No. 9; Sep. 2014.

S.D. March et al., "Focused and Deep Brain Magnetic Stimulation Using New Coil Design in Mice"; 6th Annual International IEEE EMBS Conference on Neural Engineering, San Diego, California, Nov. 6-8, 2013; pp. 125-128.

* cited by examiner

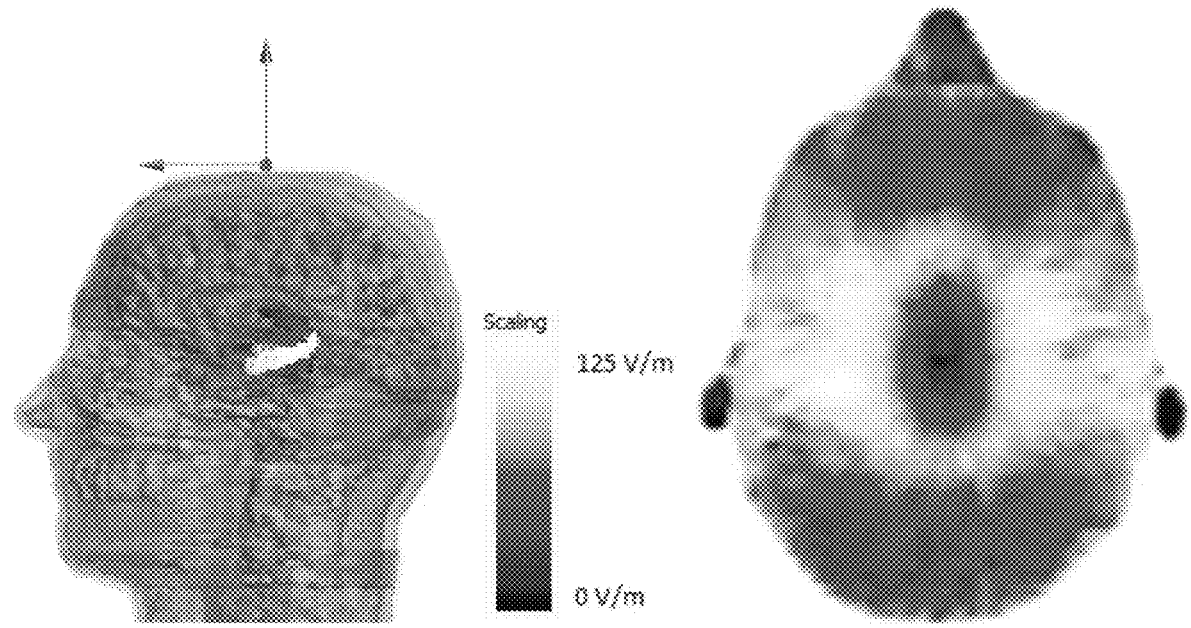
FIG. 6  FIG. 8
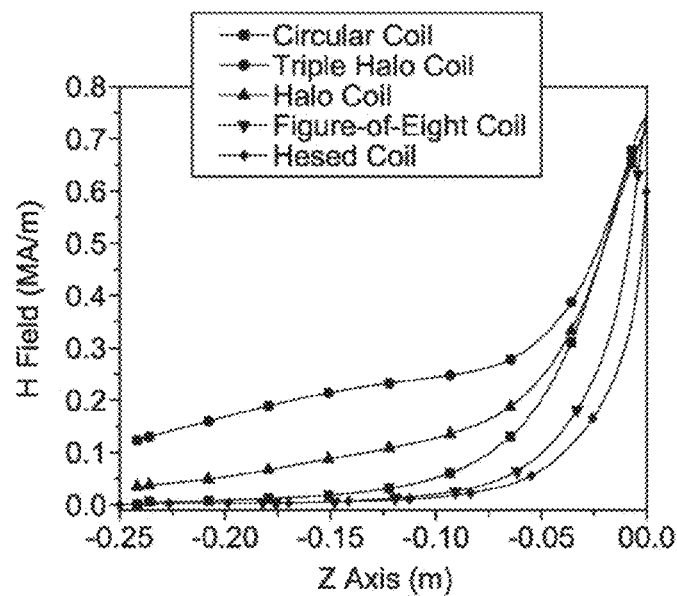
FIG. 7

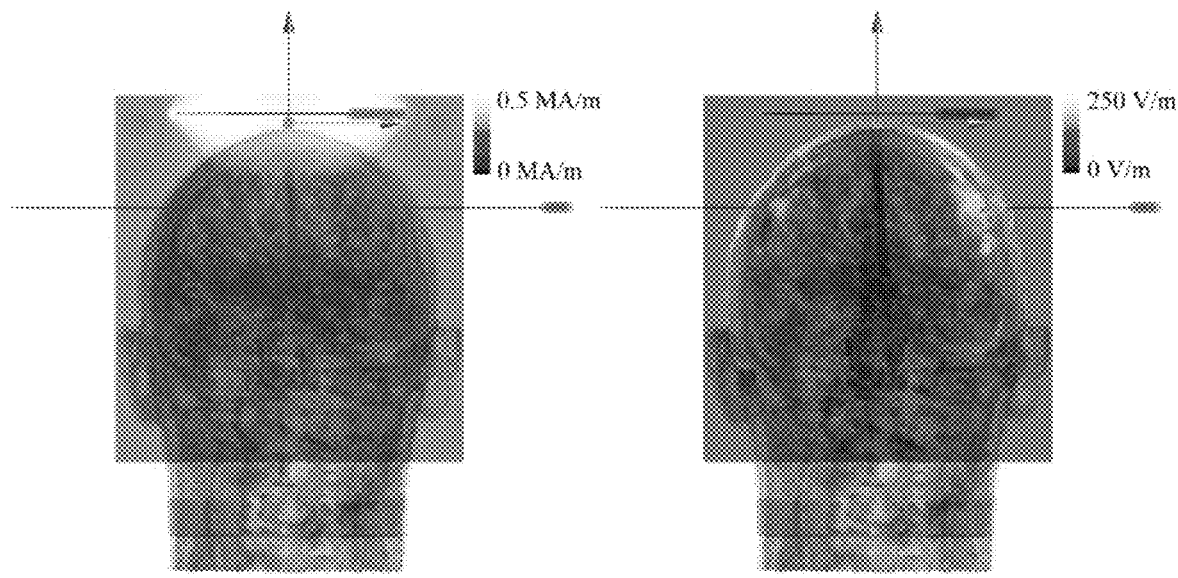
FIG. 9A  FIG. 9B
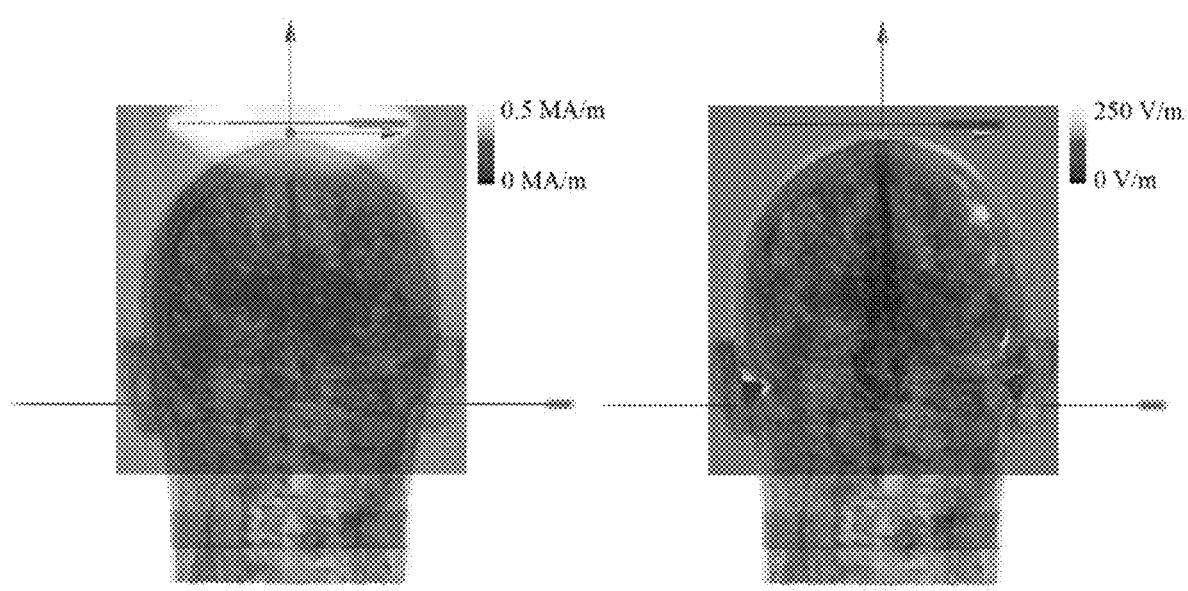
FIG. 9C  FIG. 9D

DEEP TRANSCRANIAL MAGNETIC STIMULATION APPARATUS AND METHOD

CROSS-REFERENCE TO RELATED PATENT APPLICATION

This patent application is a divisional of co-pending U.S. patent application Ser. No. 15/335,286, filed Oct. 26, 2016, which claims the benefit of U.S. Provisional Patent Application No. 62/250,571, filed Nov. 4, 2015, the entire teachings and disclosure of which are incorporated herein by reference thereto.

FIELD OF THE INVENTION

This invention generally relates to Transcranial Magnetic Stimulation (TMS), and repetitive Transcranial Magnetic Stimulation (rTMS) henceforth referred to as TMS, and more particularly to an apparatus for and method of stimulating deep regions of the brain during such TMS.

BACKGROUND OF THE INVENTION

Transcranial Magnetic Stimulation is a non-invasive method for the treatment of neurologic disorders such as depression, anxiety, Post-Traumatic Stress Disorder (PSTD), and Parkinson's disease. Time varying magnetic fields generate eddy currents in the brain. When a sufficient amount of electric potential is induced on the neurons, it causes depolarization of neuronal membrane and initiates an action potential. When TMS is administered repeatedly over a time, it is called repetitive Transcranial Magnetic Stimulation (rTMS) and these TMS pulses can inhibit or excite certain regions of the brain. Currently TMS is FDA approved for the treatment of depression.

The existing commercial TMS coils can only stimulate the superficial parts of the brain such as cortex. For successful treatment of other neurological disorders, there is a need for the development of TMS coils that can stimulate deep brain regions. Magnetic field decays rapidly with the distance from the source (coil surface), therefore it is challenging to develop TMS coils for deep brain stimulation. Moreover, magnetic fields with sufficient magnitude to stimulate the deeper regions of the brain generated by conventional TMS coils will over stimulate the surface of the brain.

What is needed, therefore, is an apparatus and method for stimulating deep brain regions during TMS without overstimulating the surface of the brain. Embodiments of the present invention provide such an apparatus and method. These and other advantages of the invention, as well as additional inventive features, will be apparent from the description of the invention provided herein.

BRIEF SUMMARY OF THE INVENTION

In one aspect, embodiments of the invention provide an apparatus and method of performing deep brain stimulation during TMS. More particularly, embodiments of the invention provide an apparatus and method of performing deep brain stimulation during TMS without overstimulating the surface of the brain.

In one embodiment a coil configuration called a "Triple Halo Coil" is utilized. This coil configuration enables stimulation of deeper regions of the brain, and in one embodiment provides 10 times higher field at a depth of 10 cm for the same amount of surface field of a standard figure of eight coil used during conventional TMS. This coil configuration is suitable for treating deep brain disorders, e.g., Parkinson's disease, PTSD, etc.

In the following discussion, an embodiment of the Triple Halo Coil will be described for deep brain stimulation and comparisons between this embodiment of the Triple Halo Coil and other standard coils, e.g. a 90 mm circular coil, figure of eight coil, "Halo Coil," and first generation Hesed coil, are provided. Magnetic and electric fields at different parts of the brain due to an embodiment of the Triple Halo Coil are also compared with that of other coils.

In one embodiment it has been found that the field in the deep brain regions such as thalamus, hypothalamus, hippocampus, and mid-brain generated by the Triple Halo Coil has increased many folds when compared to the commercial available coils such as circular coil and figure of eight coil. With the use of embodiments of the Triple Halo Coil and methods, deep brain regions related to the neurological disorders such as Parkinson's disease can be treated non-invasively, which is not possible with the commercially available coils.

Preferably, an apparatus for transcranial magnetic stimulation (TMS) of deep regions of a patient's brain includes a top coil configured to produce a magnetic field suitable for transcranial magnetic stimulation, and at least one coil configured to produce at least one off-plane magnetic field and positioned relative to the top coil to enhance the magnetic field from the top coil to stimulate deep regions of the brain. By "off-plane magnetic field" it is meant a magnetic field that is angularly offset from the field generated by the top coil and/or a magnetic field that may be moved relative to the field generated by the top coil.

In one embodiment the at least one coil is a Triple Halo Coil having a first coil positioned parallel to a plane of the top coil, a second coil positioned at +30° relative to the first coil, and a third coil positioned at −30° relative to the first coil. In other embodiments, the coils are parallel to one another (i.e., oriented 0° relative to one another) such that coils are stacked and vertically disposed from one another and/or have a variable distance between one another. In still other embodiments, the coils are arranged 90° with respect to each other such that they are perpendicular to each other. Notwithstanding the foregoing, the coils can be arranged at angles relative to each other that are intermediate of those discussed above such that the coils can be adjusted to meet the requirements of a variety of specific purposes. Preferably, each of the first coil, the second coil, and the third coil of the Triple Halo Coil is elliptical. In one embodiment, each of the first coil, the second coil, and the third coil of the Triple Halo Coil has an eccentricity of approximately 0.68. This eccentricity can be varied to lessen the stimulation at certain outer parts of the head or non-targeted parts of stimulation. Indeed, the eccentricity can be varied to include zero in certain embodiments resulting in circular coils. As such, as used herein the term elliptical is meant to include any eccentricity, including zero. In a particular embodiment, each of the first coil, the second coil, and the third coil of the Triple Halo Coil includes five windings. However, fewer or more windings can be utilized depending on the current-carrying capacity of the material used to make the windings and on the magnetic field requirements for a particular application.

In embodiments of the present invention, the three coils may be electrically isolated or coupled. In one embodiment, two of the first coil, the second coil, and the third coil of the Triple Halo Coil are electrically coupled in series. In another embodiment the first coil, the second coil, and the third coil of the Triple Halo Coil are electrically coupled in series. Alternatively, the first coil, the second coil, and the third coil of the Triple Halo Coil are electrically coupled in parallel.

In other embodiment of the present invention, a method of generating an enhanced magnetic field includes the steps of generating a first magnetic field via a first coil, generating a second magnetic field via a second coil positioned at +30° relative to the first coil, and generating a third magnetic field via a third coil positioned at −30° relative to the first coil. Preferably, the method further includes the step of generating a fourth magnetic field via a fourth coil positioned in a plane parallel to a plane of the first coil and linearly offset therefrom.

In another embodiment of the present invention, a "Variable Halo Coil" configuration with a circular coil fixed on top of the head and with vertical and/or rotational movement of a larger coil to selectively stimulate different regions of the brain is provided, along with a method and controller that accurately controls the movement and rotation of the larger coil.

Preferably, the Variable Halo Coil movable relative to the top coil. In one embodiment the Variable Halo Coil is linearly moveable perpendicular to a plane of the top coil, while in another embodiment the Variable Halo Coil is rotationally movable about an axis parallel to a plane of the top coil. In such an embodiment, the Variable Halo Coil is rotationally moveable +/−30°. Alternatively, the Variable Halo Coil is linearly moveable perpendicular to a plane of the top coil and rotationally movable about an axis parallel to a plane of the top coil.

In one embodiment of the present invention, the coil configured to produce the off-plane magnetic field is positioned in a first plane that is angularly offset +30° relative to a second plane of the top coil. Alternatively, the coil configured to produce the off-plane magnetic field is positioned in a first plane that is angularly offset −30° relative to a second plane of the top coil.

Other aspects, objectives and advantages of the invention will become more apparent from the following detailed description when taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings incorporated in and forming a part of the specification illustrate several aspects of the present invention and, together with the description, serve to explain the principles of the invention. In the drawings:

FIG. 6 shows the surface electric field in the deep brain regions (thalamus, hypothalamus, hippocampus, and mid brain) as a result of stimulation by the Triple Halo Coil;

FIG. 7 illustrates a comparison of the magnetic Field between Triple Halo Coil and other commercial coils along the Z axis, through the vertex of the heterogeneous head model showing a significant improvement of the magnetic field at 10 cm below the surface of the head with the Triple Halo Coil with the field is increased by 10 times when compared with the Figure of eight coil;

FIG. 8 depicts the surface electric field on top of the head created by the Triple Halo Coil;

FIGS. 9A and 9C illustrate the magnetic field and FIGS. 9B and 9D illustrate the electric field generated in the anatomically realistic human head model for different vertical positions of the large coil for an embodiment of the Variable Halo Coil (in FIGS. 9A and 9B, the distance between two coils is 5 cm, and in FIGS. 9C and 9D, the distance between two coils is 15 cm)

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1A:
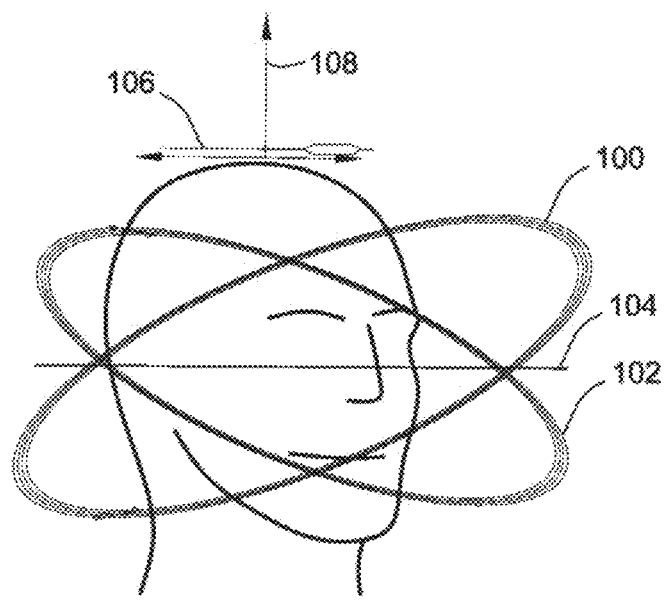
FIGS. 1A and 1B illustrate one embodiment of the Triple Halo Coil configuration along with a 90 mm circular coil positioned on top of a representative patient's head.

Turning now to the drawings wherein like elements are identified by like numerals, and in particular to FIG. 1A, there is illustrated an embodiment of a Triple Halo Coil used for deep brain stimulation during TMS. More specifically, FIG. 1A illustrates one embodiment of the Triple Halo Coil configuration along with a 90 mm circular coil positioned on top of a MRI-derived heterogeneous head model. However, as will be recognized by those skilled in the art from the following description, such embodiments are provided by way of example only, and not by way of limitation. Indeed, the device of the present invention may be used in other embodiments in which the stimulation of deep brain regions is important or desired. Still further, while the embodiment of FIG. 1A illustrates the use of the Triple Halo Coil along with a 90 mm circular coil, those skilled in the art will recognize from the following description that other TMS coil designs, e.g. other sizes of circular coils, figure of eight coils, and Hesed coils, etc., may be used with the Triple Halo Coil, or no such conventional TMS coil at all, and that all such alternative embodiments are reserved herein.

In the following description certain simulation data will be discussed with regard to the operation and effects of embodiments of the present invention. In these simulations the magnetic fields generated by the coils and induced electric field in the brain are calculated on a heterogeneous head model using a finite element analysis tool, i.e., SEMCAD X. Low frequency solver, based on the magneto-quasi static method, is used for solving the electric and magnetic fields. The heterogeneous head model used in these simulations is developed by IT'IS Foundation. This model is generated from MRI data of a 34 year old male adult and it consists of 44 differentiated tissues. The differentiated tissues are assigned with their corresponding electric and magnetic properties. In the simulations to be discussed below, the AC coil supply frequency is 2500 Hz and the current in the Triple Halo Coils is 5000 A. For the accurate comparison the simulation settings, such as voxels settings, are kept constant for all the coils.

For a quasi-static model, the magnetostatic vector potential can be calculated by the Biot-Savart law as shown in equation (1).

$$\vec{A}_o(\vec{r}) = \frac{\mu_o}{4\pi} \int_\Omega \frac{\vec{J}_o(\vec{r})}{|\vec{r}-\vec{r}'|} d\vec{r}' \qquad (1)$$

The vector potential A is decoupled from the electric field E, which is calculated by equation (2)

$$\vec{E} = j\omega\vec{A} + \nabla\varphi = \vec{E}_g + \vec{E}_i \qquad (2)$$

In one embodiment the Triple Halo Coil configuration includes three larger coils 100, 102, 104 placed around the head, along with a coil 106 positioned above the head, e.g. the 90 mm circular coil shown in FIG. 1A. The coils 100, 102, 104 of this embodiment of the Triple Halo Coil are elliptical in shape as may be seen from the top view illustration of FIG. 1B. While other coil configurations are contemplated, e.g. spherical, the elliptical coil configuration of this embodiment reduces the stimulation on the face of the patient, while still providing a sufficient amount of stimulation in the required parts of the brain. In the embodiment illustrated in FIG. 1B, the eccentricity of the elliptical coils is 0.68, with the inner radii of the elliptical coils at 110 mm and 150 mm. Other eccentricities and radii are also possible depending on the patient head size and configuration and the magnetic field generation desired.

Figure 1B:
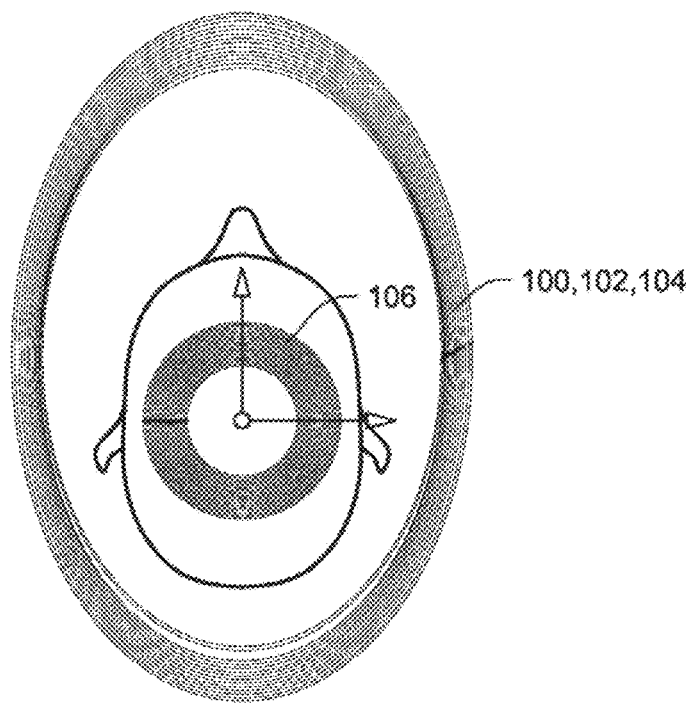

In the embodiment illustrated in FIG. 1, each of the three coils 100, 102, 104 comprise a number of windings in order to generate the desired magnetic field. In an embodiment, each coil 100, 102, 104 includes five windings, although more or fewer windings may be used as desired. Generally, the number of winding required is dependent upon the material being used for the coils, i.e., fewer windings may be needed for materials that have a higher current carrying capacity, while more windings may be needed for materials that have a lower current carrying capacity. Moreover, the number of windings can also depend on the magnetic field strength required for a particular application. Further, as will be discussed more fully below, the number of windings in each individual coil 100, 102, 104 may be the same or different. In the illustrated embodiment, however, there are a total of fifteen windings in the Triple Halo Coils. As may best be seen in FIG. 1A, these coils 100, 102, 104 are oriented at +30°, −30°, and 0° relative to the horizontal plane (assuming the patient's head is oriented along the vertical axis 108). With a fifteen winding embodiment, therefore, five windings are at 0 degrees, five windings at +30 degrees, and five windings at −30 degrees with respect to "y" plane as shown in FIG. 1A. In the embodiment depicted, the distance between the windings is 2.5 mm irrespective of the angle between the coils; however, in other embodiments, the distance between the windings can be greater or less than 2.5 mm. The center of the Triple Halo Coil in this embodiment is 110 mm from the surface of the head in 'z' axis as best shown in FIG. 1B.

The Triple Halo Coil may be a continuous design utilizing a single, continuous wire formed into the three groupings of windings positioned as discussed above and shown in FIG. 1A, or it may be constructed from a number of individual coils electrically connected as discussed below and physically orientated as shown. While various types of wire may be used in the different embodiments of the present invention, the embodiment discussed herein utilizes a rectangular cross section copper wire having a 2 mm×3 mm cross section, although embodiments of the invention are not limited thereby.

In embodiments constructed as a continuous design, all of the individual coils 100, 102, 104 are fed from a single electrical source. The windings forming the individually oriented coils 100, 102, 104 may form such coils in series, i.e. all windings forming a first coil, followed by all windings forming the second coil, followed by all windings forming the third coil. Alternatively, the individual windings may be physically positioned such that the formation of the coils 100, 102, 104 is integrated, e.g. a first winding is oriented as required by a first coil, a second winding as required by a second coil, a third winding as required by a third coil, and then repeating or reversing or otherwise interleaving until all windings forming all coils are completed.

In embodiments that utilize individually constructed coils, the electrical connection of them may be series or parallel if fed from a single electrical source. However, the individual coils 100, 102, 104 may also be unconnected and fed from individual electrical sources. In this later embodiment, the magnetic fields generated by each individual coil 100, 102, 104 may be individually controlled via its source (current, frequency, phase) and/or the number of windings in the coil. Alternative embodiments may also utilize two of the coils coupled or formed together, either in series or parallel, fed from a single source, and one coil unconnected to the other two and fed from its own source to vary the magnetic fields as desired.

Figure 2:
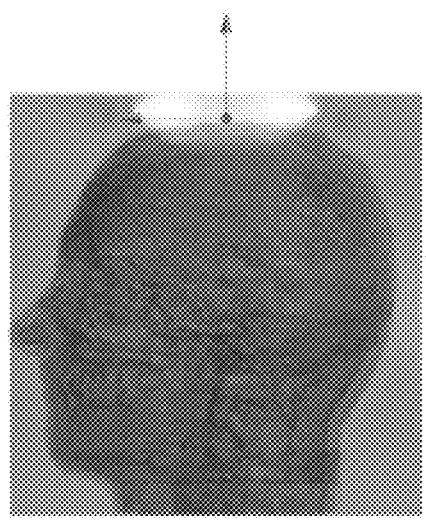
FIG. 2 shows the magnetic field through the vertex of the head generated by the Triple Halo Coil.

With an understanding of the physical construction of various embodiments of the present invention, attention will now be directed to the simulation results shown in FIGS. 2 through 6. In each of these figures, a particular parameter generated by the embodiment of the Triple Halo Coil illustrated in FIGS. 1A and 1B, e.g. the magnetic field through the vertex of the head as shown in FIG. 2, is discussed in relation to that same parameter generated by the conventional Halo Coil, by a circular coil, by the figure of eight coil, and by the Hesed coil.

Turing now to FIG. 2, the magnetic field is calculated and the comparison of the results has been done with the different types of coils mentioned above as shown in the sagittal view of the inhomogeneous head model. As may be seen in FIG. 2, there is a significant amount magnetic field in the deep brain regions due to the Triple Halo Coil. By comparison, the magnetic fields produced by the Halo Coil, a circular coil, figure of eight coil, and Hesed coil drop off respectively until the magnetic field is nearly zero in the deep brain regions of the brain for the Hesed coil. However, the magnetic field is about 0.5 MA/m in the mid brain regions generated by Triple Halo Coil.

Figure 3:
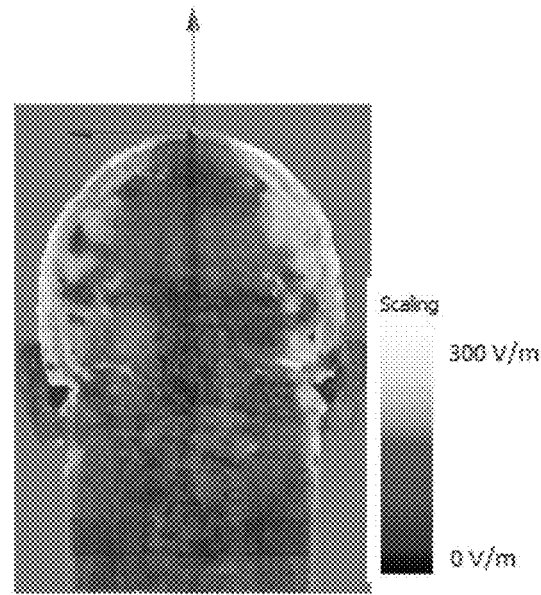
FIG. 3 shows the electric field in the coronal plane, sliced through the vertex of the head when stimulated by the Triple Halo Coil.

FIG. 3 shows the Electric field through the coronal view of the heterogeneous head model. The electric field was maximized inside the head model when stimulated by the Triple Halo Coil when compared with the Halo coil, a circular coil, figure of eight, and the Hesed coil inside the head. The Maximum electric field value below the 10 cm from the surface of the head was 280 V/m for the Triple Halo Coil as compared to and 145 V/m for the next closest configuration, the Halo Coil.

Figure 4:
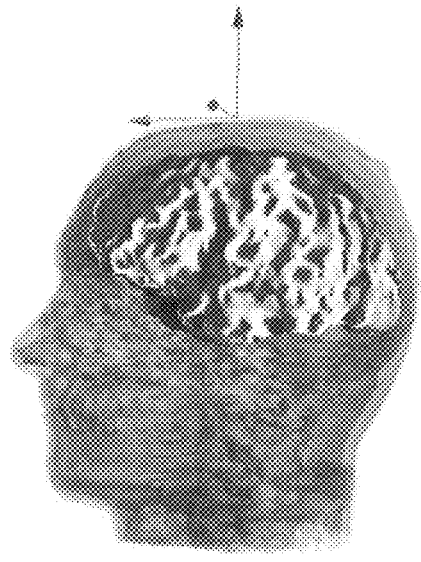
FIG. 4 shows the surface electric field in the grey matter as a result of stimulation by the Triple Halo Coil.
Figure 5:
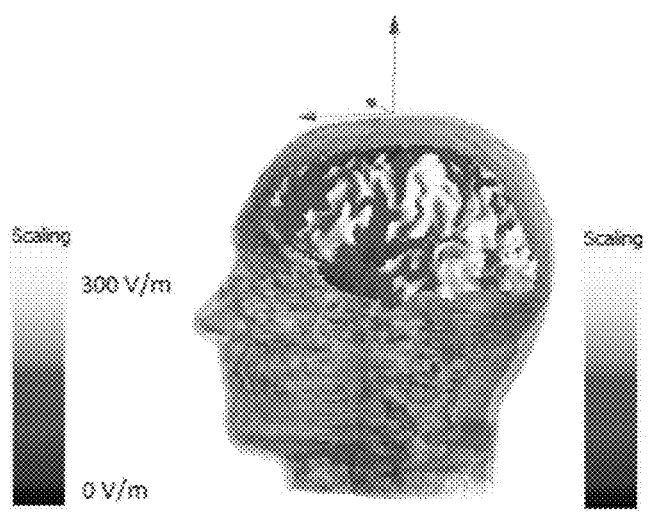
FIG. 5 shows the surface electric field in the white matter as a result of stimulation by the Triple Halo Coil.

Stimulation of motor cortex region or grey matter is shown in FIG. 4. The circular coil and figure of eight coil have been widely used for the treatment of depression by stimulating the left dorsolateral pre-frontal cortex. The figure of eight coil stimulates only the cortical regions of the brain, but as may be seen from FIG. 4, the Triple Halo Coil stimulated all the regions of the brain with a higher magnitude of electric field. The inventors surmise that this will improve the treatment effect for deep brain disorders. Stimulation of the white matter is shown in FIG. 5, which also follows the same trend as that of the grey matter.

Deep brain regions that are responsible for important cognitive and motor functions such as thalamus (which controls the motor systems of the brain), hypothalamus (which governs the physiologic functions), hippocampus (which is associated with the memory), and the mid-brain (which consists of substantia nigra, where the death of dopaminergic neurons causes Parkinson's disease) can be treated non-invasively with TMS. The stimulation of these parts is not possible with the commercially available coils due to their fast decay of the magnetic field from the surface of the coil/head. With the help of the Triple Halo Coil, the deep brain region was stimulated as shown in FIG. 6, which shows the surface electric field in the deep brain regions (thalamus, hypothalamus, hippocampus, and mid brain). Based on FIG. 6, the inventors surmise that the Triple Halo Coil will enable the treatment of neurological disorders related to these areas which is not possible with the use of commercially available coils.

The decay rate of the magnetic field from the surface of the coil to the bottom of the brain is compared with the different types of the coils along the Z axis, through the vertex of the heterogeneous head model, as shown in FIG. 7. In generating these results, the circular and figure of eight coils were kept 5 mm above the surface of the head. FIG. 7 depicts that the decay rate of the Triple Halo Coil is significantly lower than the other coils. The difference between the magnetic field generated by Triple Halo Coil and the circular coil is significantly higher in the deeper regions. To wit, at 10 cm below the surface of the head, the magnetic field generated by the circular coil and figure of eight coils was equal to 0.017 MA/m, but the magnetic fields generated by the Halo coil and the Triple Halo Coil was about 0.123 MA/m and 0.278 MA/m, respectively. Further, it can be seen that the magnetic field generated by Triple Halo Coil below 15 cm is significant where as for other coils, it became negligible.

Also as may be seen from this FIG. 7, there is an improvement of 10 times in the magnetic field at 10 cm below the surface of head between the figure of eight coil and Triple Halo Coil and an improvement of 10 times in the magnetic field at 15 cm below the surface of head between the circular coil and Triple Halo Coil. This improvement increases with the distance from the surface of the head, increasing to 25 times at 25 cm below the surface of the head.

The magnetic field generated by the top coils interacts constructively with the magnetic field generated by larger coils surrounding the head and hence reduces the decay rate compared to single top coil. The larger coils surrounding the head in the Triple Halo Coil increase the magnetic field significantly in the deeper regions of the brain. FIG. 8 shows the surface electric field produced by the Triple Halo Coil, which was maximized when compared to the other coil types. Table 1 provides a comparison between the different coils listed in column one. The second and third columns provide exact values of the magnetic field at 15 cm and 10 cm, respectively, below the surface of the head due to different coil configurations.

TABLE 1

Properties of different coil configurations

| Coil Design | H Field at 15 cm below the surface of the head | H Field at 10 cm below the surface of the head |
| --- | --- | --- |
| Triple Halo Coil | 215,865 A/m | 278,726 A/m |
| Halo Coil | 81,691 A/m | 123,608 A/m |
| Circular Coil | 21,688 A/m | 46,620 A/m |
| Figure of Eight Coil | 17,017 A/m | 17,086 A/m |
| Hesed Coil | 3,560 A/m | 12,562 A/m |

While the above description of the Triple Halo Coil embodiment of the present invention clearly shows the significant improvement to the deep brain stimulation enabled thereby, in another embodiment of the present invention selective deep brain stimulation is provided by energizing less than all of the larger coils, and in one embodiment only a single of the larger coils. Indeed, in one such alternate embodiment only a single variable position coil is used along with a graphical user interface system that enables the larger coil to rotate along the transverse plane. In one embodiment, the system can also accommodate vertical movement of the larger coil. Thus, this Variable Halo coil configuration can stimulate different regions of the brain by adjusting the position and orientation of the larger coil on the head.

This embodiment of the Variable Halo coil illustrated utilizes a circular coil fixed on top of the head and, with vertical and/or rotational movement of the larger coil to selectively stimulate different regions of the brain. During the stimulation, two stimulators were utilized to send AC current signals to the two coils. One stimulator sends an AC current with a frequency of 2.5 kHz and an amplitude of 2500 A to the circular coil. The other stimulator sends AC current with a frequency of 2.5 kHz and an amplitude of 5000 A to the larger coil. A graphical user interface (GUI) system was used to accurately control the movement and rotation of the larger coil using an Arduino microcontroller.

Figure 10A:
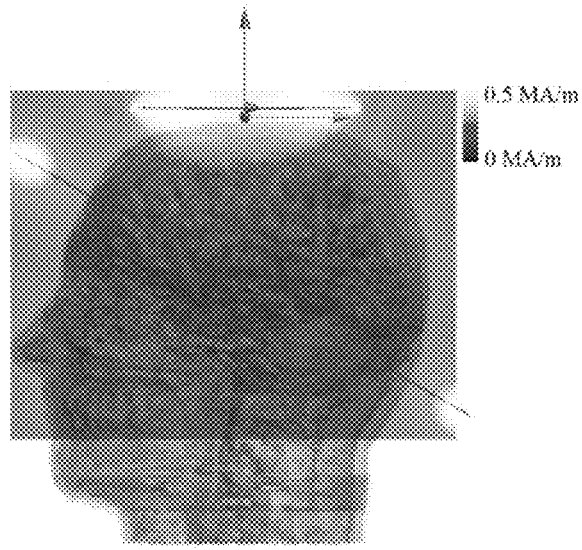
FIGS. 10A and 10C illustrate the magnetic field and FIGS. 10B and 10D illustrate the electric field generated in the anatomically realistic human head model for different rotational angles of the large coil for an embodiment of the Variable Halo Coil (in in FIGS. 10A and 10B, the coil is rotated +30°, and in FIGS. 10C and 10D, the coil is rotated)−30 °.
Figure 10B:
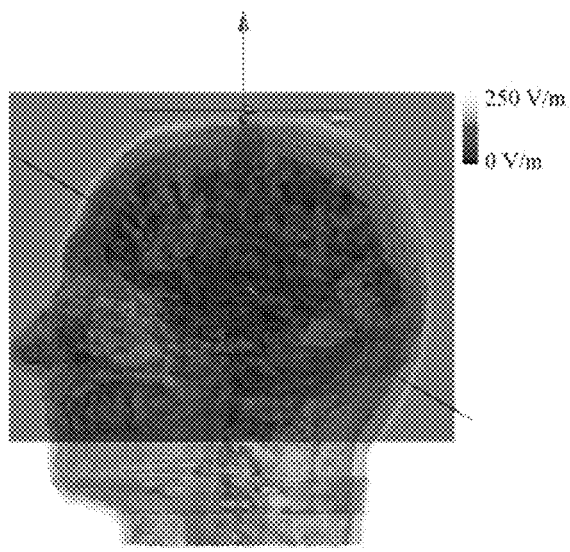
Figure 10C:
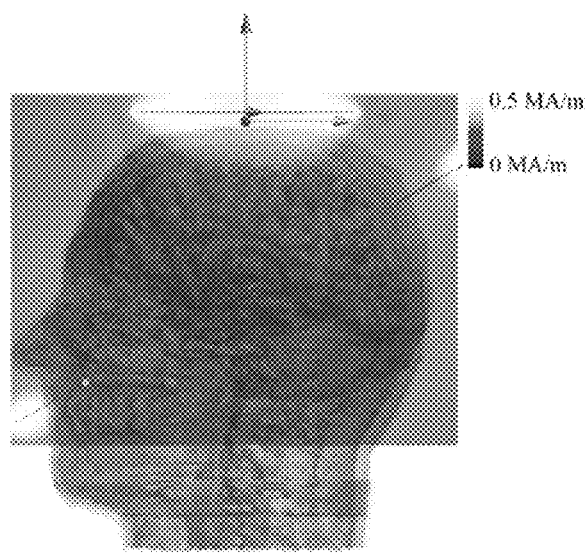
Figure 10D:
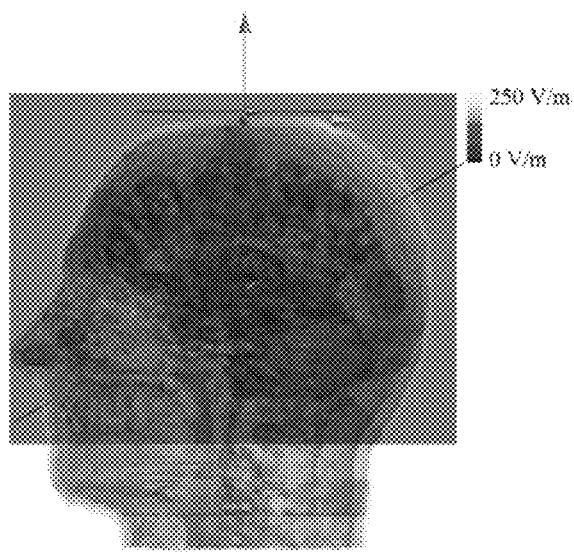

FIGS. 9A-9D show the difference in electric and magnetic fields generated in the head for different vertical positions of the large coil. When comparing FIGS. 10B and 10D, the electric field in FIG. 10B is higher than that in FIG. 10D. However, the electric field in the lower part of the head model is higher in FIG. 10D than in FIG. 10B, which was enhanced by the position of the large coil. These modeling results show the evidence that the larger coil enhances the electric and magnetic fields at the deeper regions of the brain by reducing the decay of field generated by the smaller circular coil which is fixed on the top of head. Thus, different vertical positions of the larger coil enable stimulation of different deeper regions of the human brain and help clinicians to vary the site of stimulation according to the disorder that is being treated.

FIGS. 10A-10D show the induced electric field in the anatomical heterogeneous head model with the rotational movement of the larger coil. According to FIGS. 10B and 10D, the position of the peak value of the electric field was different according to different positions of the larger coil and the peak value of electric field was approximately 250 V/m. Therefore, rotation of the larger coil also reduces the decay of the electric and magnetic fields generated by the small circular coil in a manner similar to the vertical movement of the larger coil.

As mentioned above, a GUI was developed in Java to control the movement and rotation of the larger coil with a computer via an Arduino microcontroller. The left portion of the interface included a control panel, which has two buttons to control the vertical movement of large coil by a linear actuator. The range of vertical movement was set to be from +5 cm to −5 cm compared to its origin with a step size of 1 cm. The control panel also includes two buttons to control the rotation of the large coil by a servo motor. The range of rotation was set to be from +30° to −30° compared to its origin with a step size of 5°. The right portion of the interface provides modeling results of the electric and magnetic fields for the selected position of the large coil. These images are configured to show the distribution of magnetic and electric fields, which indicate the site of stimulation with a field larger than the threshold or peak field for the selected position of the large coil.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus for transcranial magnetic stimulation (TMS) and repetitive transcranial magnetic stimulation (rTMS) of deep regions of a patient's brain, comprising:
    a top coil configured to be positioned over a top of the patient's head and configured to produce a magnetic field suitable for transcranial magnetic stimulation;
    at least one coil configured to produce at least one off-plane magnetic field and positioned relative to the top coil to enhance the magnetic field from the top coil to stimulate deep regions of the brain; and
    wherein the at least one coil comprises a Variable Halo Coil movable relative to the top coil, the Variable Halo Coil being sized and shaped such that the Variable Halo Coil is capable of encircling the patient's head within the Variable Halo Coil; and
    wherein windings of each coil of the at least one coil are disposed in a same plane and such that the windings are configured to encircle the patient's head.

2. The apparatus of claim 1, wherein the Variable Halo Coil is linearly moveable perpendicular to a plane of the top coil.

3. The apparatus of claim 1, wherein the Variable Halo Coil is rotationally movable about an axis parallel to a plane of the top coil.

4. The apparatus of claim 3, wherein the Variable Halo Coil is rotationally moveable +/−30°.

5. The apparatus of claim 1, wherein the Variable Halo Coil is linearly moveable perpendicular to a plane of the top coil and rotationally movable about an axis parallel to a plane of the top coil.

6. The apparatus of claim 1, wherein the Variable Halo Coil is elliptical.

7. The apparatus of claim 6, wherein the Variable Halo Coil has an eccentricity of approximately 0.68.

8. The apparatus of claim 1, wherein the Variable Halo Coil includes at least five windings.

9. The apparatus of claim 1, wherein the at least one coil configured to produce the at least one off-plane magnetic field is positioned in a first plane that is angularly offset +30° relative to a second plane of the top coil.

10. The apparatus of claim 1, wherein the at least one coil configured to produce the at least one off-plane magnetic field is positioned in a first plane that is angularly offset −30° relative to a second plane of the top coil.

11. An apparatus for transcranial magnetic stimulation (TMS) and repetitive transcranial magnetic stimulation (rTMS) of deep regions of a patient's brain, comprising:
    a top coil configured to be positioned over a top of the patient's head and configured to produce a magnetic field suitable for transcranial magnetic stimulation; and
    at least one coil configured to produce at least one off-plane magnetic field and positioned relative to the top coil to enhance the magnetic field from the top coil to stimulate deep regions of the brain;
    wherein the at least one coil comprises a Variable Halo Coil movable relative to the top coil; and
    wherein the at least one coil comprises a first coil positioned parallel to a plane of the top coil, a second coil positioned at +30° relative to the first coil, and a third coil positioned at −30° relative to the first coil, and wherein any one of the first coil, the second coil, or the third coil forms the Variable Halo Coil.

12. An apparatus for transcranial magnetic stimulation (TMS) and repetitive transcranial magnetic stimulation (rTMS) of deep regions of a patient's brain, comprising:
    a top coil configured to be positioned over a top of the patient's head and configured to produce a magnetic field suitable for transcranial magnetic stimulation; and
    at least one coil configured to produce at least one off-plane magnetic field and positioned relative to the top coil to enhance the magnetic field from the top coil to stimulate deep regions of the brain;

wherein the at least one coil comprises a Variable Halo Coil movable relative to the top coil; and wherein the at least one coil comprises a first coil positioned parallel to a plane of the top coil, a second coil positioned at +30° relative to the first coil, and a third coil positioned at −30° relative to the first coil, and wherein any two of the first coil, the second coil, or the third coil forms the Variable Halo Coil.

13. A method of generating an enhanced magnetic field for transcranial magnetic stimulation (TMS) and repetitive transcranial magnetic stimulation (rTMS) of deep regions of a patient's brain, comprising the steps of:

generating a magnetic field via a first coil encircling the patient's head within the first coil, the first coil being a single layer comprising a plurality of windings disposed in a same plane;

generating a further magnetic field via a top coil positioned over a top of the patient's head in a plane parallel to a plane of the first coil and linearly offset therefrom.

14. The method of claim 13, wherein the method further comprises the step of linearly moving the first coil perpendicular to a plane of the top coil.

15. The method of claim 13, wherein the method further comprises the step of rotationally moving the first coil about an axis parallel to a plane of the top coil.

16. A method of generating an enhanced magnetic field for transcranial magnetic stimulation (TMS) and repetitive transcranial magnetic stimulation (rTMS) of deep regions of a patient's brain, comprising the steps of:

generating a magnetic field via a first coil encircling the patient's head within the first coil, the first coil comprising a plurality of windings disposed in a same plane;

generating a further magnetic field via a top coil positioned over a top of the patient's head in a plane parallel to a plane of the first coil and linearly offset therefrom;

wherein the method further comprises the step of rotationally moving the first coil about an axis parallel to a plane of the top coil; and wherein the step of rotationally moving comprises the step of rotationally moving the first coil +/−30°.

17. The method of claim 13, wherein the method further comprises the step of moving the first coil linearly perpendicular to the plane of the top coil and rotationally about an axis parallel to the plane of the top coil.

18. The method of claim 13, wherein the steps of generating the magnetic field and generating the further magnetic field further comprise the step of generating only the magnetic field and the further magnetic field.

\* \* \* \* \*